United States Patent
Carter et al.

(10) Patent No.: US 6,205,360 B1
(45) Date of Patent: Mar. 20, 2001

(54) APPARATUS AND METHOD FOR AUTOMATICALLY DETERMINING STIMULATION PARAMETERS

(75) Inventors: Paul Michael Carter, Carlingford; David Kerry Money, Pennant Hills, both of (AU)

(73) Assignee: Cochlear Limited, Lane Cove (AU)

( * ) Notice: Subject to any disclaimer, the term of this patent is extended or adjusted under 35 U.S.C. 154(b) by 0 days.

(21) Appl. No.: 09/029,365

(22) PCT Filed: Sep. 6, 1996

(86) PCT No.: PCT/AU96/00558

§ 371 Date: Mar. 4, 1998

§ 102(e) Date: Mar. 4, 1998

(87) PCT Pub. No.: WO97/09863

PCT Pub. Date: Mar. 13, 1997

(30) Foreign Application Priority Data

Sep. 7, 1995 (AU) .................................... PN5331

(51) Int. Cl.[7] ...................................................... A61N 1/36
(52) U.S. Cl. ................................................................ 607/57
(58) Field of Search ......................................... 607/56, 57

(56) References Cited

U.S. PATENT DOCUMENTS 4,532,930 * 8/1985 Crosby et al. ........................ 607/57
5,758,651 * 6/1998 Nygard et al. ........................ 607/57

OTHER PUBLICATIONS

"Electrically Elicited Stapedius Reflex In Cochlear Implant Patients"—Ear and Hearing vol. 11, No. 5, 1990; Battmer et al.*

"Acoustic Reflex In Patients With Cochlear Implants"—American Journal of Otology vol. 12, Supplement 1991; Stephan et al.*

"Prediction Of Dynamic Range For The Stapedius Reflex In Cochlear Implant Patients"—Ear and Hearing, vol. 9, No. 1 (1988); Jerger et al.*

"Electrically Evoked Auditory Brainstorm Responses (EABR) And Middle Latency Responses (EMLR) Obtained From Patients With The Nucleus Multi–Channel Cochlear Implant"—Ear and Hearing vol. 11, No., 1; Shallop et al.*

"Prediction Of Behavioral Threshold And Comfort Values For Nucleus 22–Channel Implant Patients From Electrical Auditory Brain Stem Response Test Results"—Annals of Otology, Rhinology, & Laryngology, vol. 100, No. 11 (Nov. 91); Shallop et al.*

* cited by examiner

*Primary Examiner*—William E. Kamm
(74) *Attorney, Agent, or Firm*—Gottlieb Rackman & Reisman PC

(57) ABSTRACT

Disclosed is an arrangement allowing for automatic calculation of stimulation parameters, for example dynamic ranges for stimulation, in an auditory prosthesis, for example a multichannel cochlear implant. The arrangement includes, in a preferred form, an electrode 12 for detecting activity of the stapedius muscle, and uses the electrode array 5 to sense neural response to stimulation, so that a maximum comfortable stimulation level and threshold level for each channel can be determined. The process may be initiated by the implantee, avoiding the requirement for external equipment and extensive audiological testing.

46 Claims, 7 Drawing Sheets

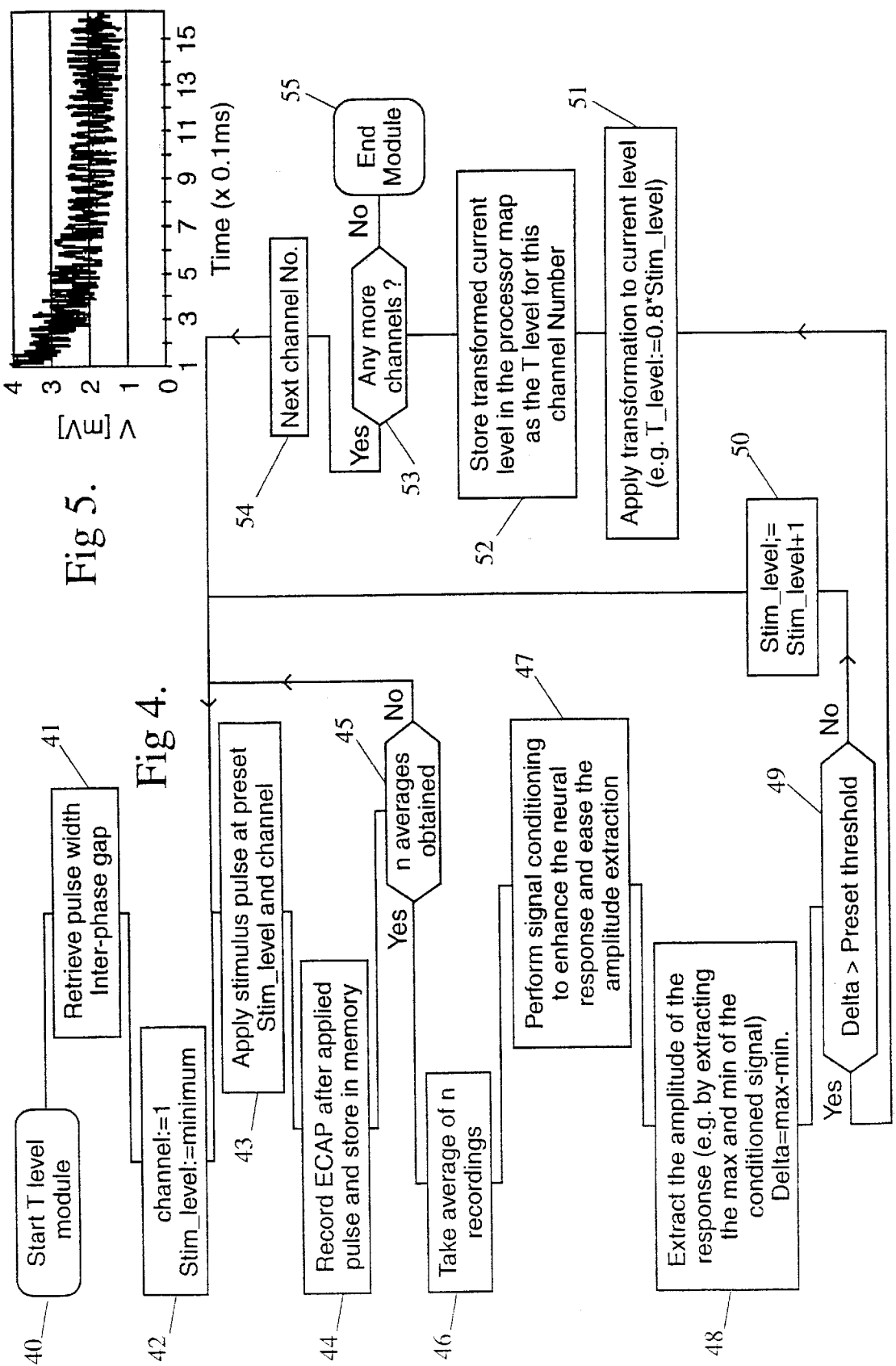

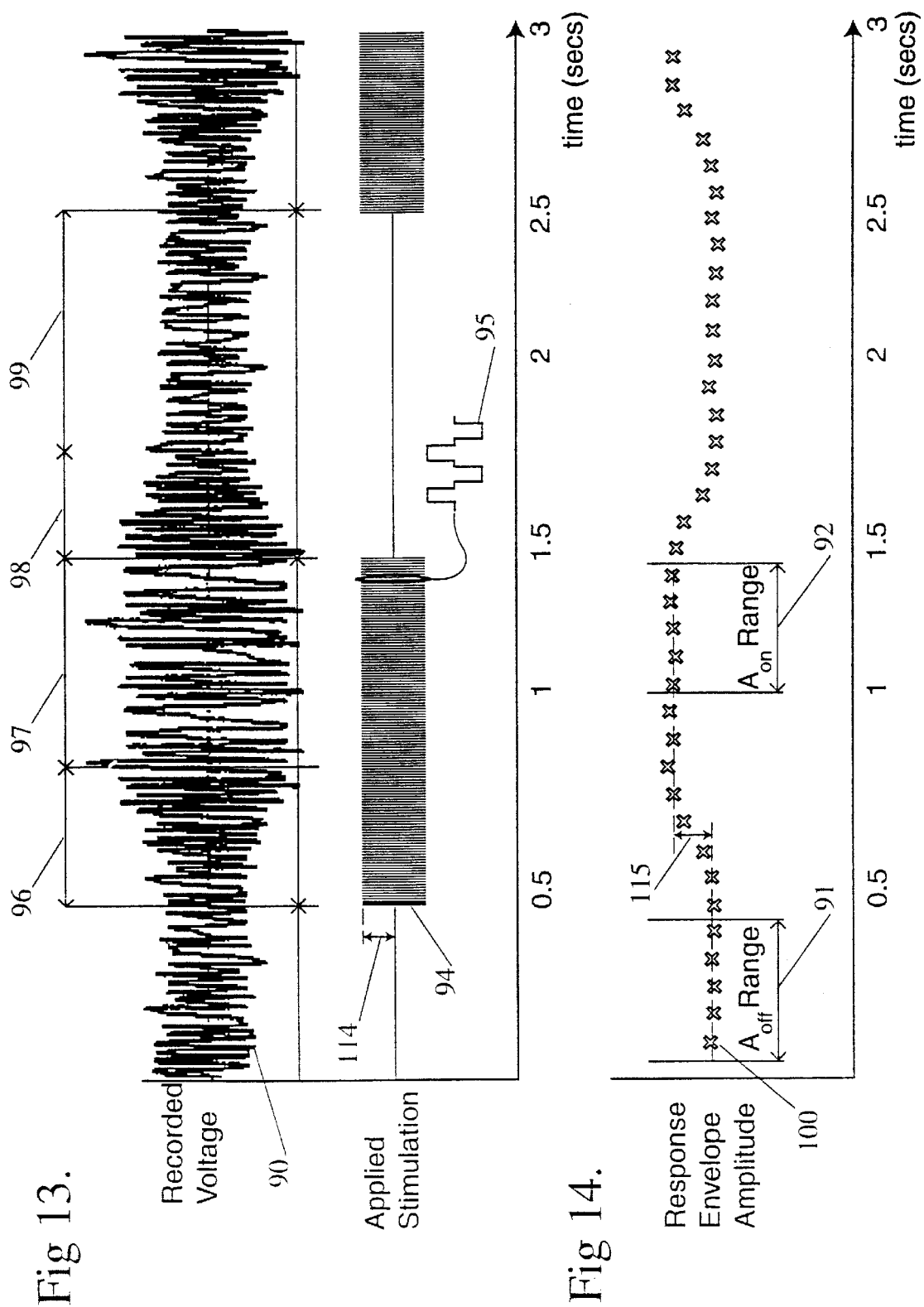

APPARATUS AND METHOD FOR AUTOMATICALLY DETERMINING STIMULATION PARAMETERS

TECHNICAL FIELD

The present invention relates to auditory prostheses, particularly but not exclusively cochlear implants.

BACKGROUND ART

The present invention relates generally to auditory prostheses, but will be principally described in relation to multi-channel cochlear implants. Such an implant conventionally consists of three components—an implanted electrode array, an implanted receiver/stimulator unit (RSU) and an externally worn speech processor. The speech processor receives sound signals, for example via a microphone, processes them so as to produce a set of signals corresponding to stimuli, then communicates these signals to the RSU. Communication between the speech processor and the RSU may be by an inductive link, a direct cable, or any other suitable means. The RSU, in accordance with the received signals, provides electrical stimulation signals to the electrode array.

For each implantee, it is necessary to set the dynamic range of the stimulus pulses presented by the electrode array in order to optimally and comfortably enhance speech perception by the implantee. The dynamic range is generally set between two parameters—the threshold level (T), being the minimum amount of electrical stimulation that is required to elicit a perceived sound from the implantee, and the comfort (C) level, defined as the maximum amount of electrical stimulation which can be applied before the patient reports discomfort. The T and C levels typically vary for each channel in a multichannel implant.

Conventional setting of the dynamic range uses an elaborate audiometric process, heavily reliant upon patient responses, to set T & C levels. A particular difficulty exists in relation to children, who are often unable to provide meaningful indications as to their perceptions and responses to various stimuli. Moreover, it would be desirable to allow patients to reset the dynamic range using an automatic process, as required, so that physiological variations in their perception can be accounted for. Some of these variations are routine—for example, commonly dynamic range will vary during a woman's menstrual cycle, or may vary with medication or illness. The present system for dynamic range setting requires the services of a trained audiologist in a clinic, and hence cannot provide routine resetting when required by the patient.

Various workers have examined the use of either the stapedius reflex or various evoked action potentials with a view to objectively setting speech processors.

The stapedius muscle, when contracted, acts as a dampening mechanism on the ossicular chain within the ear. In the normally functioning ear, contraction of the stapedius attenuates the vibration transmitted through the malleus, incus and stapes to the oval window, so as to prevent overstimulation of the auditory system. A survey of the prior art shows that the general approach to measuring the stapedius reflex has been to use an acoustic probe, placed in the ear contralateral to the applied stimulation, in order to measure the muscle's response via the mechanical impedance of the tympanic membrane. This approach allows for accurate measurement of the response of the stapedius but is not appropriate for implementation in an implanted device.

For example, Battmer et al. (Electrically Elicited Stapedius Reflex in Cochlear Implant Patients—Ear and Hearing Vol. 11, No. 5, 1990), investigated the use of stapedius reflex evaluations for objective setting of cochlear implant speech processors. In contrast to the present invention they recorded the stapedius muscle's response to electrical stimulation of the cochlea by means of a contralateral acoustic impedance meter. The level of contraction of the stapedius muscle was used to determine both the T and C level.

In a paper by Stephan et al ("Acoustic Reflex in Patients with Cochlear Implants" American Journal of Otology Vol 12, Supplement 1991) the authors indicated that psychoacoustic tests relying on evoked auditory responses and electrically elicited acoustic stapedius reflexes were of use in setting the patient's speech processor. However, that paper taught that acoustic reflex testing using contralateral detection is recommended over electrophysiologic methods because of the difficulties associated with overcoming the difficulties presented by artefacts in the electrophysiological methods.

In a paper by Jerger et al, in Ear and Hearing, vol 9, No 1 (1988), entitled "Prediction of dynamic range for the stapedius reflex in cochlear implant patients", amplitude growth functions for an electrically-elicited stapedius reflex were compared with behavioural estimates of dynamic range. This paper concluded that comfort levels are typically greater than or equal to the saturation or plateau, level of stapedius response. The stapedius reflex, whilst electrically elicited, was measured using an external acoustic probe arrangement.

In a 1990 paper by Shallop et al ("Electrically Evoked Auditory Brainstorm Responses (EABR) and Middle Latency Responses (EMLR) Obtained from Patients with the Nucleus Multi-Channel Cochlear Implant" Ear and Hearing Vol 11, No. 1) the technique of using EABR measurements to set dynamic range was investigated. The author's conclusion was that EABR and EMLR measurements correlate better with comfort levels than with threshold levels. In a paper by Shallop et al ("Prediction of Behavioural Threshold and Comfort Values for Nucleus 22 Channel Implant Patients from Electrical Auditory Brain Stem Response Test Results", Annals of Otology, Rhinology, & Laryngology, vol 100, No 11 (Nov 91)) the authors again discussed and investigated prediction of behavioural threshold and comfort level values using EABR procedures. In both of these papers, the neural response is obtained via a second monitoring mechanism not associated with the implant, and later correlated. The authors state that they are "cautious" about inferring T and C levels to be expected from speech from EABR and EMLR recordings.

None of these papers disclose an arrangement, in which the parameter is electrically measured, and this measurement is directly input to the receiver stimulator unit for use in deriving dynamic range. Moreover, these papers do not disclose any arrangement which could automatically adjust dynamic range without input from skilled personnel.

It is an object of the present invention to provide an arrangement in which at least one of the dynamic range parameters are automatically derived and processed, without the necessity for the implantee's perceptions to be subjectively assessed. It is a further object of the present invention to provide an auditory prosthesis arrangement in which the dynamic range parameters are able to be automatically reset by the implantee without the need for specialised external equipment and personnel.

SUMMARY OF THE INVENTION

According to a first aspect the present invention provides an auditory prosthesis including processing means for providing electrical stimulus signals to a stimulation means, said prosthesis including a sensor means adapted to sense physiological response to applied stimulation, said sensor means communicating with said processing means, and memory means communicating with said processing means to provide values for stimulation parameters to said processing means so that said processing means can define appropriate stimulus signals, wherein signals from said sensor means are processed by said processing means in accordance with a predetermined algorithm, so as to determine at least one stimulation parameter for at least one stimulation mode of said device, said value being stored in said memory means.

According to another aspect the present invention provides an auditory prosthesis including processing means for providing electrical stimulus signals to a stimulation means, said prosthesis including a sensor means adapted to sense neural response correlating to an acoustic percept, said sensor means communicating with said processing means, and memory means communicating with said processing means to provide values for stimulation parameters to said processing means so that said processing means can define appropriate stimulus signals, wherein signals from said sensor means are processed by said processing means in accordance with a predetermined algorithm, so as to define a threshold stimulation level for at least one stimulation mode of said device, said value being stored in said memory means. Preferably, the neural response sensed is the EAP response of the basilar membrane.

According to a further aspect, the present invention provides an auditory prosthesis including processing means for providing electrical stimulus signals to a stimulation means, said prosthesis including sensor means adapted to sense activity of the stapedius muscle, said sensor means communicating with said processing means, and memory means communicating with said processing means to provide values for stimulation parameters to said processing means so that said processing means can define appropriate stimulus signals, wherein signals from said sensor means are processed by said processing means in accordance with a predetermined algorithm, so as to define a maximum comfortable stimulation level for at least one stimulation mode of said device, said value being stored in said memory means.

Preferably, the sensor means are arranged so as to electrically sense activity of the stapedius muscle. The sensor may be an electrode on or adjacent to the stapedius muscle.

According to another aspect, the present invention comprises an auditory prosthesis adapted to automatically derive threshold and maximum comfortable stimulation levels so as to determine a dynamic range for electrical stimuli, said prosthesis including processing means for providing electrical stimulus signals to a stimulation means, first sensor means adapted to sense activity of the stapedius muscle, second sensor means adapted to sense a neural response correlating to an acoustic percept, and memory means communicating with said processing means to provide values for stimulation parameters to said processing means so that said processing means can define appropriate stimulus signals, said first and second sensor means communicating with said processing means, wherein signals from said sensor means are processed by said processing means in accordance with a predetermined algorithm, so as to define a threshold stimulation level and a maximum comfortable stimulation level for at least one stimulation mode of said device, said value being stored in said memory means.

The present invention further relates to the methods for setting parameters in relation to the dynamic range of auditory prostheses, and to systems incorporating these methods.

In its broadest form, the present invention is concerned with providing an auditory prosthesis which includes sensors communicating with a processing means so that the stimulation parameters of the prosthesis can be modified in response to the sensed response to the stimuli presented. It is envisaged that various stimulation parameters could be controlled in this way, avoiding the need for subjective, labour intensive adjustment of the parameters, and allowing the patient to select when these parameters need adjustment and perform the adjustment on demand.

In a preferred implementation, the inventors proposes the use of electrically measured neural responses as a direct input to stimulation processor so as to define the dynamic range of an auditory prosthesis for a given patient. In a preferred aspect, the inventive device uses a combination of evoked neural potentials and electrically measured activity of the stapedius muscle to determine dynamic range without subjective assessment. Various workers have examined the use of either the stapedius reflex or various evoked action potentials with a view to objectively setting speech processors. This work has not contemplated providing an automatic system for use by the patient alone. The prior art cited above shows that the general approach to measuring the stapedius reflex has been to use an acoustic probe, placed in the ear contralateral to the applied stimulation, in order to measure the muscle's response via the mechanical impedance of the tympanic membrane. This approach allows for accurate measurement of the response of the stapedius but is not appropriate for the portability and convenience facilitated by the present invention.

BRIEF DESCRIPTION OF DRAWINGS

An implementation of the present invention will now be described with reference to the accompanying figures, in which:

FIG. 4 is a flow chart of the procedure for determining the T levels

FIG. 5 is a graph of the typical electrical activity measured in response to stimulation of the basilar membrane by the cochlear electrode array

FIG. 13 is a timing diagram of the typical electrical activity of the stapedius muscle measured in response to applied stimulation of the basilar membrane.

FIG. 14 is a graph of the envelope of the typical electrical activity of the stapedius muscle measured in response to applied stimulation of the basilar membrane.

DETAILED DESCRIPTION

The present invention is described in the context of a multichannel cochlear implant. However, the principle of the present invention is applicable to related devices, including totally implanted devices, direct neural stimulation, and other auditory prostheses which are intended to produce a neural response to stimulation. Similarly, other or more stimulation parameters than dynamic range could be controlled using the principle of the present invention. Alternative sensors could be used to the stapedius activity and evoked response measurement via the electrode array which are proposed—for example, a separate evoked response array.

The illustrative embodiment of the present invention makes use of an extracochlear electrode from a conventional receiver stimulator unit of a cochlear implant to monitor stapedius muscle activity. The intracochlear electrodes are used to monitor the electrical status of the auditory nerve. Both evoked action potential (EAP) of the auditory nerve and stapedius reflex information are telemetered back from the receiver stimulator to the wearable speech processor. The speech processor includes integral hardware and software to test for comfort and threshold setting levels by using the telemetered information, and applying a predefined algorithm, which will be discussed below. This enables levels to be set automatically by the patient at the press of a button. It will be appreciated that whilst this division between the processing functions of the receiver stimulator unit and the speech processor is convenient in terms of current cochlear implant technology, alternative implementations could be used, for example in the case of a fully implantable device. The location of the processing step is not critical to the general principles of the present invention.

Figure 1:
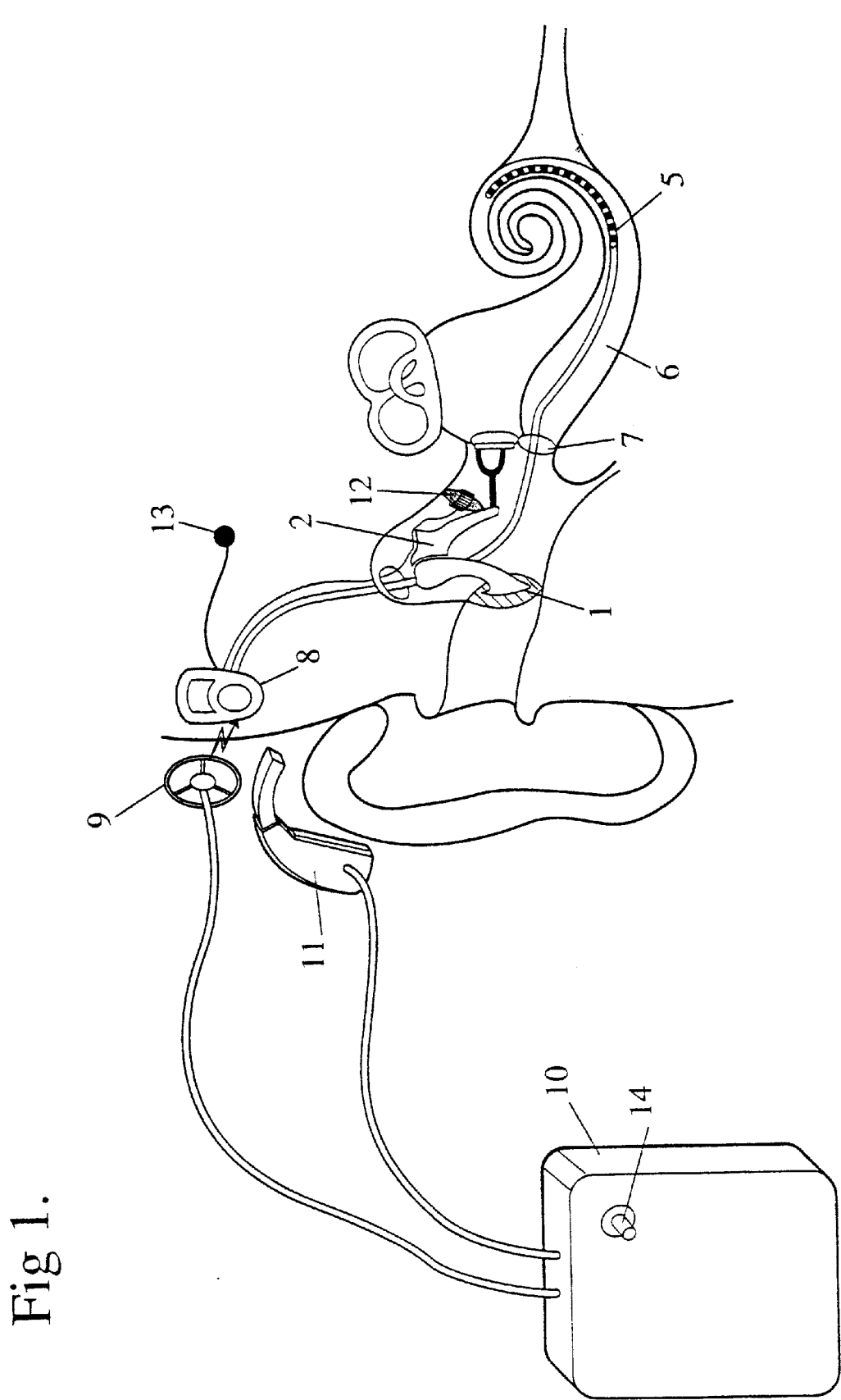
FIG. 1 is a schematic diagram of the arrangement of a cochlear implant system incorporating the invention.

Referring to FIG. 1, the relevant anatomical features of the ear are illustrated. In the normally functioning ear, the tympanic membrane 1 vibrates in response to ambient sound, and via the ossicular chain 2 the vibration is transferred to the oval window 3. The stapedius muscle 4 operates in the normal ear to contract and hence damp mechanically the transmission of vibrations to the oval window 3. An electrode array 5 is shown implanted via conventional surgical procedures, inserted within the scala tympani 6 via the round window 7, and connected to the implanted receiver stimulator unit 8. Receiver-stimulator unit 8 communicates via an RF link with RF coil 9 and hence the speech processor 10. A microphone 11, illustratively mounted behind the pinna 25, provides sound signals to the speech processor. The implant described to this point is essentially a conventional arrangement.

A further stapedius monitoring electrode 12 is attached to the stapedius muscle 4. This provides signals indicative of stapedius reflex activity. It may be attached either to the belly of the muscle or to the tendon which is a surgically easier point of attachment, or to any suitable site which enables a signal indicative of stapedius activity to be detected.

According to the preferred implementation of the present invention, the neural response of the auditory nerve 26 and basilar membrane 27 evoked by stimulation may be monitored using the implanted electrode array 5. Thus, the implanted array 5 is used both to provide stimuli, and to measure the response to such stimuli during the period between stimuli. Such a monitoring arrangement and telemetering arrangement is described in Australian patent application No. 56898/94 by the present applicant, the disclosure of which is hereby incorporated by reference.

The stimulations are delivered by means of a number of "channels". For example, the delivery of a stimulation current between two particular electrodes of the array may be defined as a stimulation via channel 1. Similarly other combinations of electrodes involved in stimulation delivery will also define other stimulation channels. Extra-cochlear electrode 13, which is also used in some conventional arrangements, is used as the reference electrode in measuring the evoked action potential of the auditory nerve and the electrical activity of the stapedius.

The EAP response, detected by the electrode array 5, and the response of the stapedius, monitored by the stapedius monitoring electrode 12, are detected by the receiver stimulator unit 8 relative to the reference electrode, and then telemetered back to the speech processor. As in known arrangements speech processor 10 sends signals via the RF link to receiver stimulator unit 8, which then provides stimulus pulses via the electrode array in accordance with the commands sent by speech processor 10.

Figure 2:
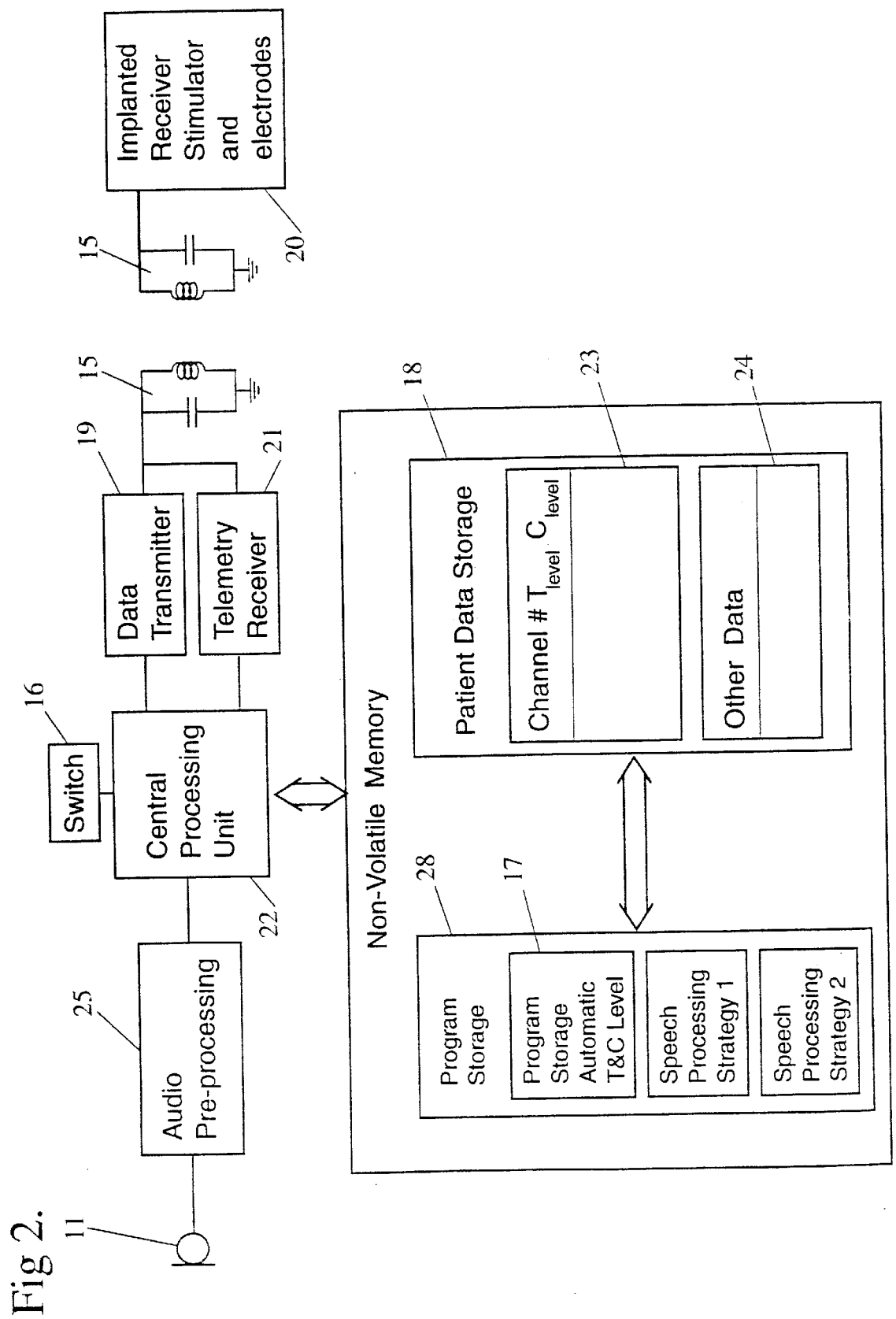
FIG. 2 is a block diagram of a device according to a first embodiment of the invention.

T&C switch 14 is pressed by the patient to initiate the T&C level setting procedure. FIG. 2 shows the components of the device in block form, including microphone 11, audio pre-processing 25, central processing unit (CPU) 22, and transcutaneuous link 15.

With reference to FIG. 2 the operation of the present invention will now be described. On pressing the T&C switch 16 the CPU 22 is directed to automatically calculate the patient's required T and C levels. Initially the Automatic T&C Level Program 17 is retrieved from program storage memory 28. The CPU then steps through the program. Firstly the system is put into a telemetry mode whereby the response of the auditory nerve to stimulation can be monitored. The CPU transmits the code for a stimulus pulse via the data transmitter 19 and transcutaneous link 15. The transmission contains information as to which electrodes are to deliver the stimulation and the stimulation amplitude and duration which are retrieved from the patient data storage memory 24. The received transmission is decoded by the receiver-stimulator 20 and the prescribed stimulation is applied. The evoked action potential of the auditory nerve in response to the stimulation is monitored by the receiver-stimulator and telemetered back to the telemetry receiver 21 via the transcutaneous link 15. This procedure is repeated several times and the recorded data is conditioned and tested for significance as will be explained subsequently. At the end of this procedure a figure is reached for the EAP response derived threshold level of the implantee. It has been found experimentally that the stimulus level which elicits a definite EAP response is significantly higher than the T level derived by subjectively testing patients. Accordingly the final T level value is derived from the final stimulation level after suitable adjustment and then stored as an entry in the patient data storage T&C level table 23. The entire procedure is then repeated for all stimulation channels.

Once the T levels have been calculated for each stimulation channel those levels are used as a starting point for calculating the C levels. In the previously described manner the CPU transmits the code for a stimulus pulse via the data transmitter 19 and transcutaneous link 15. The first stimulation pulse is transmitted with a stimulation level equal to the T level for the stimulation channel. The electrical activity of the stapedius muscle is measured both when there is and when there is not application of stimulation and by a method which will shortly be described in more detail the C level for each stimulation channel is determined. These levels are stored as entries in the patient data storage T&C level table 23.

Figure 3:
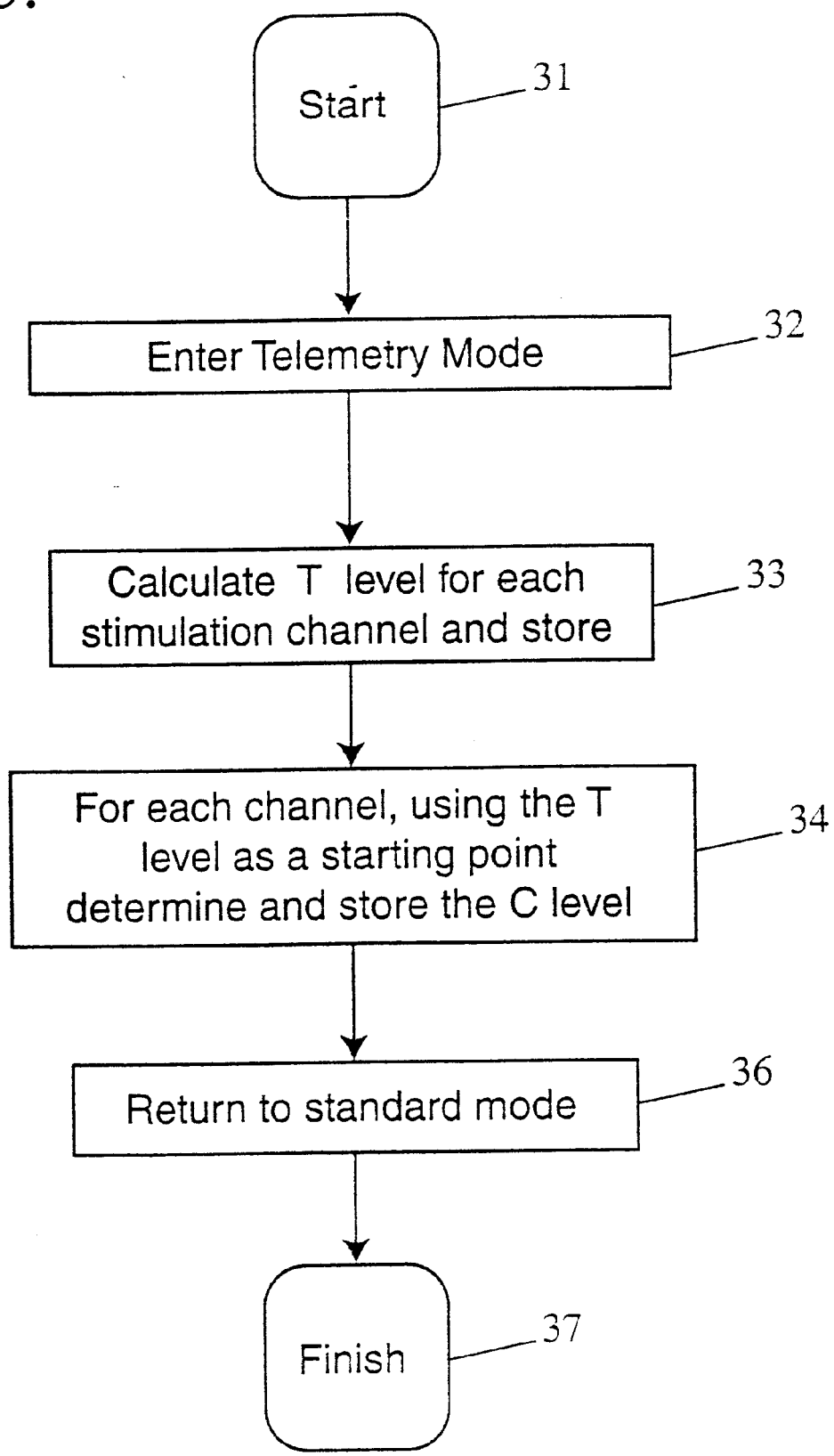
FIG. 3 is a flow chart of the procedure for determining the T and C levels.

The overall operation of the invention which has now been described is depicted as a flow chart in FIG. 3. After startup 31 the system enters telemetry mode 32 as the information regarding the electrical activity of the auditory nerve and the stapedius muscle are to be sent to the speech processor. The T levels are then calculated for each channel and stored in the T&C level table at step 33. Using the T levels as a starting point the C levels are then derived for each channel and similarly stored in the T&C level table 34. The cochlear implant then returns to normal operation 36 using the newly defined dynamic range. The T&C level setting program then ends 37.

The details of box 33 will now be described. The steps involved in the process of determining the T levels are shown diagrammatically in FIG. 4 which is a flowchart of the process. Before entering a first loop relevant stimulation parameters including pulse width and inter-phase gap duration are retrieved from memory. The number of the channel whose T level is to be derived is set to one and the stimulation level that is to be applied is set to a minimum level which has been empirically found to be below that capable of evoking an auditory nerve response. Alternatively the minimum current level could simply be set to zero.

A single stimulus pulse is then delivered at the minimum amplitude by channel 1. Any response to the stimulus pulse is telemetered back to the CPU 22 according to 44. The procedure then cycles through blocks 45, 43 and 44 until several responses have been measured. At the end of this process the average of the readings is stored according to 46. The values stored at 46 represent the EAP response to the stimulation but said response is also heavily affected by an artefact due to the evoking stimulation. This artefact must be removed in order to gain an accurate value for the EAP response.

At 47 the program undertakes signal conditioning procedures in order to lessen the effects of said artefact. One previously published way of performing said conditioning is the 'double pulse' method which will be described shortly.

The amplitude of the EAP response is evaluated at 48 and stored in variable Delta. Decision box 49 tests Delta for significance against a preset value. If Delta is found to be insignificant then no T level is deemed to have been detected and so the current level of the applied stimuli is increased at 50. The process then loops until the current level is sufficiently high to enable the "Delta>Preset" threshold condition of decision block 49 to be met. In that case a stimulation level at which a significant EAP response is elicited is deemed to have been reached for the stimulation channel under test. However, as has been discussed previously it has been found experimentally that said stimulation level is significantly higher than the optimal T level and so the T level is found by reducing the value Stim_level either by means of known algorithms or by an empirically determined amount. In the embodiment of FIG. 4 the level is set at box 51 to 80% of the above threshold stimulation level. The final value of the T level is then stored as a table entry in the T&C Patient Data Storage table 23. The decision box 53 tests whether or not the T level has been found for all channels and if not then the previously described process is repeated until completion.

Figure 6:
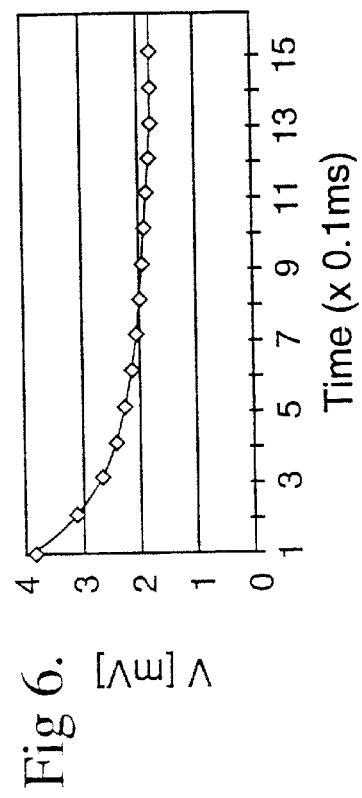
FIG. 6 is graph of the average electrical activity measured in response to stimulation of the basilar membrane by the cochlear electrode array

In order to further clarify the previous procedure the steps involved in measuring the nerve's EAP response to stimulation, items 43–48 will now be described with references to FIGS. 5–11. As stated in box 43 a stimulation is applied to the auditory nerve. In response to the applied stimulation a response of the form shown in FIG. 5 is elicited and data from said waveform is measured and telemetered to the speech processor 10. FIG. 5 shows that the response is obscured by noise. Accordingly the experiment is performed a number of times, indicated by the integer n in the present embodiment, and an average graph, as shown in FIG. 6, corresponding to the instructions of item 46 is obtained in order to reduce the obscuring effects of random noise. An example of the signal conditioning referred to in box 47 will now be explained.

Figure 7:
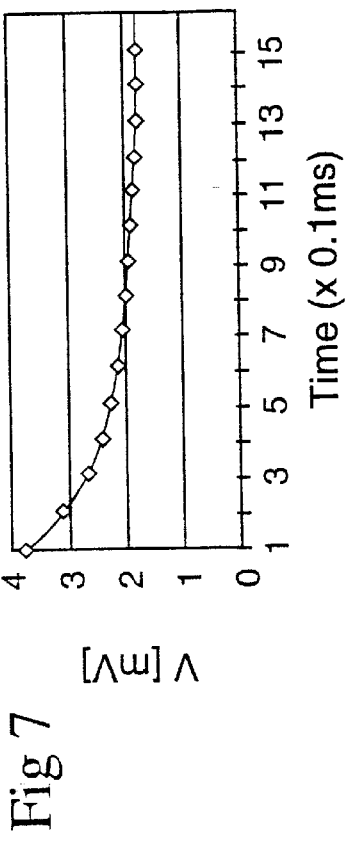
FIG. 7 is a graph of the average electrical activity measured in response to stimulation of the basilar membrane by the cochlear electrode array according to the "double pulse" method.
Figure 9:
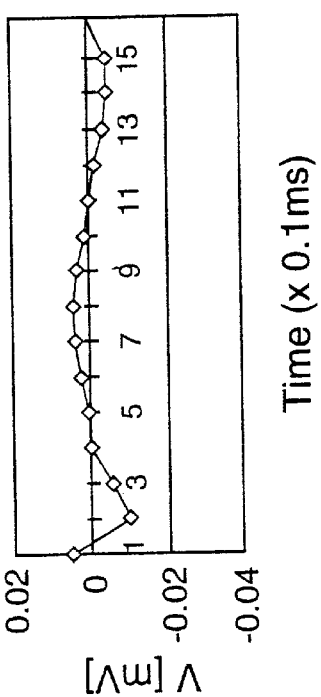
FIG. 9 is a graph of the seven point moving average of the data presented in FIG. 8.
Figure 8:
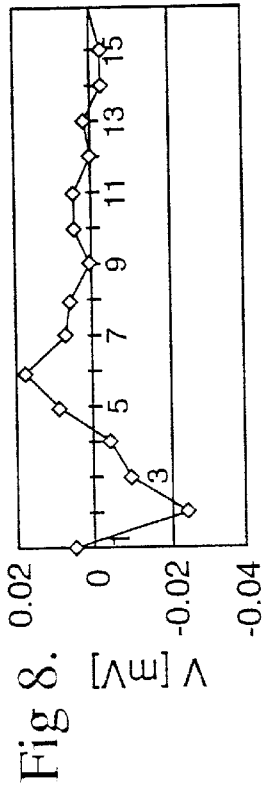
FIG. 8 is a graph of the difference between the data recorded in FIG. 7 and FIG. 6.
Figure 11:
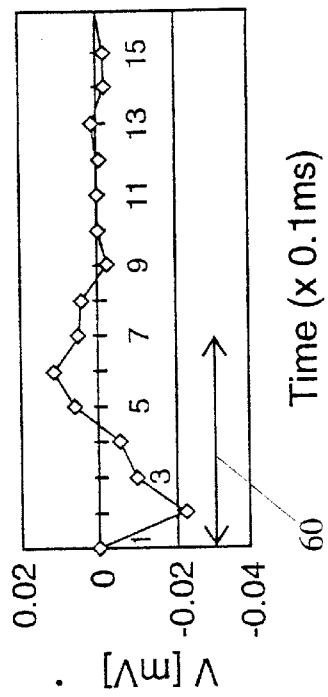
FIG. 11 is a graph of the difference in the data presented in FIG. 8 and that presented in FIG. 10.
Figure 10:
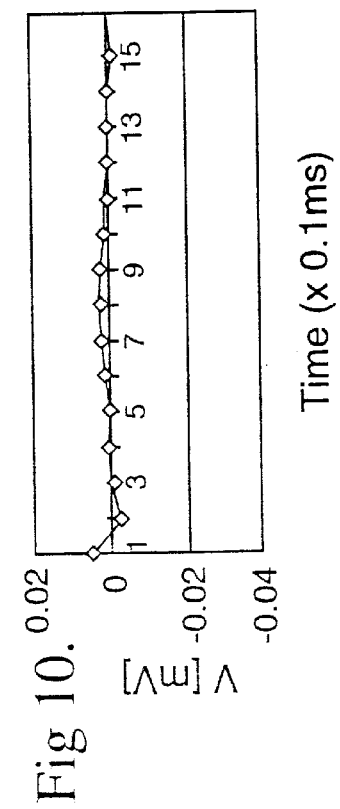
FIG. 10 is a graph of the seven point moving average of the data presented in FIG. 9.

Two successive stimulus pulses are applied about 1 ms apart. The patient's response is measured after the application of the second of the successive stimulations. The first pulse recruits the nerve so that the recording after the second pulse produces only the artefact with no neural response component present. The average waveform that is derived from repeating this procedure several times is depicted in FIG. 7. FIG. 8 is a graph of the difference between the data depicted in FIG. 7 and that of FIG. 6. That is, it is the result of subtracting the recorded artefact from the data representing the combined EAP response and artefact. In practice, even after this subtraction, there remains a small though significant amount of artefact superimposed on the neural response. The artefact consists of an exponentially decaying low frequency signal. The signal is further conditioned to enhance the fidelity of the EAP signal by twice low pass filtering the combined signal depicted in FIG. 8. The first filtering is shown in FIG. 9 and is conveniently achieved by taking a seven point moving average of the data presented in FIG. 8. Similarly the second filtering shown in FIG. 10 is simply the seven point moving average of the data in 9. Thus the signal depicted in FIG. 10 consists largely of the residual artefact. This artefact signal is subtracted from the combined EAP response and residual artefact of FIG. 8 and the resulting EAP response to the stimulation is plotted in FIG. 11. This method of extracting the EAP response from the combined response and amplitude corresponds to the step described as box 47 of the flowchart depicted in FIG. 4. Apart from the "double pulse" method other signal conditioning known in the art could also be used at box 47. The standard deviation of the data is calculated where the neural response has the greatest range, that is, across the range indicated by the double headed arrow 60. This value is proportional to the size of the EAP response. Determination of this value corresponds to the value Delta of box 48.

The previously described procedure of calculating Delta is repeated with increasing stimulation levels as indicated by box 50 until Delta is deemed to be greater than an empirically measured threshold. Said threshold is derived by testing a population of cochlear implant patients and is factory set and stored in the system memory 24. As previously described it has been found that the current level at which the first significant EAP response is detected is usually higher than the patient's actual T level and so the T level is determined to an adjusted value of Delta. This adjustment is shown at box 51 and an example is given there of simply setting the T level to 20% below the stimulation level that was found to generate a significant EAP response. Other transformations could also be used for this step and are known in the prior art, see for example Parkins and Colombo Hearing Research, 31 (1987) pp267–286.

Figure 12:
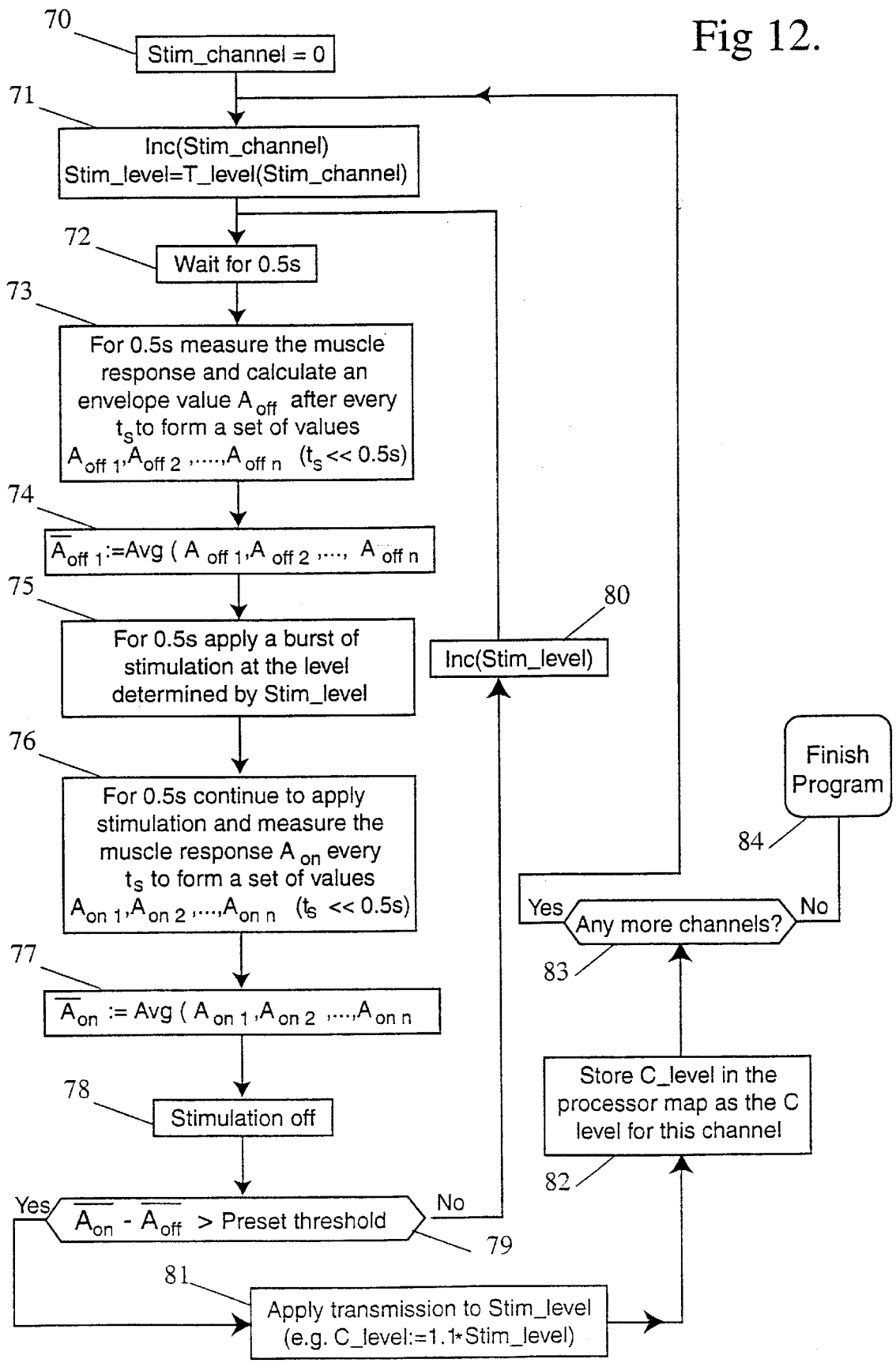
FIG. 12 is a flowchart of the procedure for calculating the C levels.

Once the T level has been determined and recorded for each stimulation channel the procedure for calculating the C level is embarked upon. The steps for doing this are shown in the block diagram of FIG. 12. Boxes 72 to 78 describe a method for determining the magnitude of the muscle's response to the application of a current of amplitude set by the variable "Stim_level" delivered by means of stimulation channel "Stim_channel". The steps dictated by each of those boxes will be described with reference to FIGS. 13 and 14.

Initially from commencement time up to the first half second no stimulation is applied in accordance with box 72. This waiting period is included to ensure that the muscle has had sufficient time to emerge from any refractory period, Throughout the next 0.5 s the electrical activity of the stapedius muscle 4 is monitored via an extra-cochlear electrode 12 placed either on, in, or near to the muscle. During this period no stimulation is applied. The activity of the muscle is frequently sampled at periods of $t_s$ secs and the average of each of the samples taken in that time are used to form a set of envelope values $A_{off1} \ldots A_{offn}$ as shown in box 73. These values are represented as crosses in the $A_{off}$ range 91. Subsequently stimulation 94 is applied at time =0.5 s up until time =1.5 s as determined by boxes 75 and 76. The stimulation consists of high frequency biphasic current pulses, typically of the form depicted by item 95 which is intended to be an enlargement of two cycles of stimulation 94. In response to application of the stimulation the electrical activity of the stapedius muscle is as shown in sections 96, 97, 98. Section 96 exhibits behaviour in accordance with the "onset" effect of the stimulation whereby the electrical activity of the muscle "ramps-up" to the plateau of section 97. Upon cessation of stimulation at time=1.5 s there is a decay of muscle activity 98 until a lower plateau region 99 is reached. In order to detect the C level the envelope of the recorded voltage 90 is detected and plotted at intervals as crosses 100. The portion of the envelope prior to cessation of the stimulation applied during period 94 is defined as the "$A_{on}$ range" 92. The average of the envelope values 100 during the $A_{on}$ range 92 is defined as $$\overline{A_{on}}.$$

Similarly the portion of the envelope 100 during the period prior to application of a burst of stimulation 91, is defined as the "$A_{off}$ range" 91. The average of the $A_{off}$ range of values is defined as $$\overline{A_{off}}.$$

In order to find the amplitude 114 of the stimulation 94 that must be applied to elicit muscle activity indicative as being in response to the patients C level, the amplitude 114 of the applied stimulation is gradually increased until the difference 115 between $$\overline{A_{on}} \text{ and } \overline{A_{off}}$$

is found to exceed a preset threshold. Said preset threshold is an empirically determined value, which can be determined from studies on a population of cochlear implant patients. Once the current level at which this significance criterion is met has been found then a transformation is applied by which the stimulation current level is increased by a small amount. It has been found that without this transformation the patient's C level is set significantly less than at an optimal level.

Items 72–78 comprise the steps of calculating a value $$\overline{A_{off}}$$

for the average level of muscle activity during the period of no stimulation 91 and the average level of muscle activity, $$\overline{A_{on}},$$

during the period of stimulation 92 at an intensity of stimulation given by 'Stim_level'. The stimulation level is tested at box 79 for significance by comparing $$\overline{A_{on}} \text{ and } \overline{A_{off}}.$$

If the difference of the two is less than the empirically derived preset threshold then the parameter Stim_level is increased at box 80 and the procedure is repeated until the Stim_level reaches a magnitude where the muscle activity, represented by $$\overline{A_{on}} - \overline{A_{off}},$$

in response to stimulation is above the preset threshold. In that case the stimulation level transformation is applied at box 81. In the present embodiment the transformation comprises setting the C_level to 10% above the first significant value of Stim_level. C_level is recorded as the C level for the stimulation channel under test and stored as part of the T&C level table in memory 23 of the processor. The whole procedure is then repeated until the C level has been derived and stored for all channels.

The system as described so far facilitates the automatic recalibration of T&C levels for all channels. The time taken to perform said recalibration is of the order of twenty minutes. It may be though that the patient desires recalibration only of the T levels or of the C levels but not both. Furthermore it may be that only some stimulation channels require recalibration and that most are operating between comfortable and detectable levels of stimulation. Therefore, a further aspect of the invention is that the user may at his or her option request calibration of only certain selected channels and either T or C levels. By reducing the extent of the recalibration the time taken to perform the operation is reduced.

The channels to be recalibrated may be designated by the user by means of a simple selection system. For example, on pressing T&C switch 14 the speech processor 10 may produce a sequential stimulation at each channel. The user could then again press switch 14 in order to request recalibration of the T and C levels for that channel. If the user did not press the switch within a short time frame then the processor would quickly move on to the next channel so that only selected channels would be recalibrated and the time taken for the overall procedure would be limited to only that needed to adjust problematic levels.

It will be appreciated that the algorithms used are merely illustrative, and alternative techniques may be used within the general concept of electrically evoked and measured parameters being used as a basis for automated level setting.

It will also be understood that the present invention contemplates either the T or C levels only being automatically set as described, with alternative techniques being used for the other of C and T levels. Preferably, however, both T and C levels are determined as set out above. It will be further understood that the present invention contemplates that the automatic procedures may be customised further by an audiologist or physician, for example to manually alter levels, fix levels for some channels independent of the automatic procedure, or utilise special rules for certain implantees.

What is claimed is:

1. An auditory prosthesis comprising:
   stimulation means adapted to apply stimulus signals to a person's ear;
   processing means for generating and providing said stimulus signals to said stimulation means in accordance with a set of stimulation parameters;
   sensor means adapted to sense a physiological response to said stimulus signals, said sensor means communicating with said processing means and generating sense signals; and
   memory means communicating with said processing means to provide said stimulation parameters to said processing means so that said processing means can define appropriate stimulus signals, wherein said processing means is constructed and arranged to process said sense signals from said sensor means in accordance with a predetermined algorithm to determine at least one of said stimulation parameters, said one stimulation parameter being stored in said memory means.

2. An auditory prosthesis according to claim 1 wherein said stimulation means is constructed and arranged to be implanted.

3. An auditory prosthesis according to claim 2, wherein said sensor means comprises a multi-electrode intracochlear array.

4. An auditory prosthesis according to claim 1 wherein said one stimulation parameter is a threshold stimulation parameter, and wherein said processing means is constructed and arranged to generate said stimulus signals with said stimulus signals having levels exceeding said threshold stimulation level.

5. An auditory prosthesis according to claim 4, wherein said processing means is arranged and constructed to perform a dynamic range setting procedure to determine a range of said stimulus signals, and wherein said signal processing means is constructed and arranged to determine said threshold stimulation level as part of said dynamic range setting procedure.

6. An auditory prosthesis according to claim 5 further comprising a command input that receives a command from the user of said prosthesis and wherein said processing means is constructed and arranged to initiate said dynamic range procedure in response to said command.

7. An auditory prosthesis according to claim 5, wherein said stimulation means includes a multielectrode array, said array characterizing channels, wherein said processing means generates stimulus signals for each of said channels in accordance with a threshold level for each of said channel, wherein said processing means is constructed and arranged to determine said threshold levels separately for each of said channels during said dynamic range setting procedure.

8. An auditory prosthesis according to claim 1, wherein said prosthesis comprises an external speech processor, and an implanted device in communication with said external speech processor and including a telemetry circuit for sending telemetry data to said speech processor including information from said sensor means, said external speech processor further including said processing means, said external speech processor being constructed and arranged to communicate said electrical stimulus signals to said implanted device.

9. An auditory prosthesis according to claim 1 wherein said sensor means is arranged and constructed to sense the auditory response of one of the auditory nerve and the basilar membrane of the user.

10. An auditory prosthesis according to claim 1, wherein said processing means is constructed and arranged to process said sense signals to determine a maximum comfortable stimulation level, said maximum comfortable stimulation level defining a maximum level for said stimulus signals.

11. An auditory prosthesis according to claim 10, wherein said processing means is arranged and constructed to perform a dynamic range setting procedure to determine a range of said stimulus signals, and wherein said signal processing means is constructed and arranged to determine said maximum comfortable level as part of said dynamic range setting procedure.

12. An auditory prosthesis according to claim 11, wherein said stimulation means includes a multielectrode array, said array characterizing channels, wherein said processing means generates stimulus signals for each of said channels in accordance with a maximum comfortable stimulation level for each of said channel, wherein said processing means is constructed and arranged to determine said maximum comfortable stimulation levels separately for each of said channels during said dynamic range setting procedure.

13. An auditory prosthesis according to claim 1, wherein the sensor means are arranged and constructed so as to electrically sense activity of the stapedius muscle.

14. An auditory prosthesis according to claim 1, wherein said sensor means includes a plurality of sensor elements to sense different physiological responses to stimuli.

15. An auditory prosthesis according to claim 14, wherein said stimulation means includes electrodes and said sensor means shares some of said electrodes.

16. An auditory prosthesis according to claim 14, wherein said sensor means further include a sensor adapted to electrically sense activity of the stapedius muscle, said sensor generating a stapedius signal.

17. An auditory prosthesis according to claim 16, wherein said stimulation means includes a multielectrode array, said array characterizing channels, wherein said processing means generates electrical stimulus signals for each of said channels in accordance with a threshold level and a maximum comfortable stimulation level for each of said channel, wherein said processing means is constructed and arranged to determine said threshold levels and said maximum comfortable stimulation levels separately for each of said channels during said dynamic range setting procedure.

18. An auditory prosthesis according to claim 17, wherein said processing means is adapted to determine said maximum comfortable stimulation level by reference to said stapedius signal and said threshold level by reference to the evoked neural response to said stimulus signals.

19. An auditory prosthesis according to claim 18, wherein said processing means is constructed and arranged to determine said threshold stimulation level and said maximum comfortable stimulation level as part of a dynamic range setting procedure.

20. An auditory prosthesis comprising:
   stimulation means arranged and constructed to apply electrical stimulation signals to a user;
   processing means for providing said electrical stimulus signals to said stimulation means;
   a sensor means adapted to sense electrical response correlating to an acoustic percept, said sensor means communicating with said processing means; and memory means communicating with said processing means to provide values for stimulation parameters to said processing means to define said stimulus signals in at least one stimulation mode, wherein sense signals are processing by said processing means in accordance with a predetermined algorithm to define a threshold stimulation level for said at least one stimulation mode, said threshold stimulation level being stored in said memory means.

21. An auditory prosthesis according to claim 20, wherein said sensor means communicates with said stimulation means.

22. An auditory prosthesis according to claim 20, wherein said stimulus means includes a multi-electrode intracochlear array.

23. An auditory prosthesis according to claim 22, wherein said prosthesis comprises an external speech processor, and an implanted device in communication with said external speech processor and including a telemetry circuit for sending telemetry data to said speech processor including information from said sensor means, said external speech processor further including said processing means, said external speech processor being constructed and arranged to communicate said stimulus signals to said implanted device.

24. An auditory prosthesis according to claim 20, wherein said processing means is arranged and constructed to perform a dynamic range setting procedure to determine a range of said stimulus signal, and wherein said signal processing means is arranged and constructed to determine said threshold stimulation level as part of said dynamic range setting procedure.

25. An auditory prosthesis according to claim 24 wherein said stimulation means includes a multielectrode array, said array characterizing channels, wherein said processing means generates stimulus signals for each of said channels in accordance with a threshold level for each of said channel, wherein said processing means is constructed and arranged to determine said threshold levels separately for each of said channels during said dynamic range setting procedure.

26. An auditory prosthesis according to claim 20, wherein said sensor means is arranged and constructed to sense the neural response of one of the auditory nerve and the basilar membrane of the user.

27. An auditory prosthesis comprising
stimulation means;
a processing means for providing electrical stimulus signals to said stimulation means;
sensor means adapted to sense electrical activity of the stapedius muscle, said sensor means communicating with said processing means by sending stapedius signals; and
memory means communicating with said processing means to provide values for stimulation parameters to said processing means, said processing means being adapted to define said stimulus signals in accordance with said values;
wherein said processing means is adapted to process said stapedius signals in accordance with a predetermined algorithm to define a maximum comfortable stimulation level, said value being stored in said memory means.

28. An auditory prosthesis according to claim 27, said stimulation means is constructed and arranged to be implanted and wherein said sensor means with said stimulation means.

29. An auditory prosthesis according to claim 27, wherein the sensor means are constructed and arranged to electrically sense activity of the stapedius muscle.

30. An auditory prosthesis according to claim 27, wherein said processing means is arranged and constructed to perform a dynamic range setting procedure to determine a range of said stimulus signal, and wherein said signal processing means is constructed and arranged to determine said maximum comfortable level as part of said dynamic range setting procedure.

31. An auditory prosthesis according to claim 30, wherein said stimulation means includes a multielectrode array, said array characterizing channels, wherein said processing means generates stimulus signals for each of said channels in accordance with a maximum comfortable stimulation level for each of said channel, wherein said processing means is constructed and arranged to determine said maximum comfortable stimulation levels separately for each of said channels during said dynamic range setting procedure.

32. An auditory prosthesis according to claim 27, wherein said prosthesis comprises an external speech processor, and an implanted device in communication with said external speech processor and including a telemetry circuit for sending telemetry data to said speech processor including information from said sensor means, said external speech processor further including said processing means, said external speech processor being constructed and arranged to communicate said stimulus signals to said implanted device.

33. An auditory prosthesis adapted to automatically derive threshold and maximum comfortable stimulation levels so as to determine a dynamic range for electrical stimuli, said prosthesis comprising:
a stimulation device;
a processor that provides electrical stimulus signals to said stimulation device;
a first sensor adapted to sense electrical activity associated with the stapedius muscle;
a second sensor adapted to sense an electrical response of nervous tissue correlating to an acoustic percept; and
a memory communicating with said processor to provide values for stimulation parameters; said processor being arranged and constructed to said stimulus signals, in accordance with said values, said first and second sensors communicating with said processor, wherein said processor is constructed and arranged to process said signals from said sensors in accordance with a predetermined algorithm to define a threshold stimulation level and a maximum comfortable stimulation level for for said stimulus signals said levels being stored in said memory.

34. An auditory prosthesis according to claim 33 wherein said stimulation device is arranged and constructed to be implanted and wherein said first and second sensors communicate with said stimulation device.

35. An auditory prosthesis according to claim 33, wherein said implanted stimulation device comprises a multi-electrode intracochlear array.

36. An auditory prosthesis according to claim 35, wherein said second sensor means comprises said multi-electrode intracochlear array.

37. An auditory prosthesis according to claim 33 wherein said processor is adapted to perform a dynamic range procedure for determining a range for said stimulus signals, said processing means being constructed and arranged to determine said threshold stimulation level and said maximum comfort stimulation level as part of said dynamic range procedure.

38. An auditory prosthesis according to claim 33, wherein said prosthesis comprises an external speech processor, and an implanted device in communication with said external speech processor and including a telemetry circuit for sending telemetry data to said speech processor including information from said first and second sensors, said external speech processor, said external speech processor being constructed and arranged to communicate said stimulus signals to said implanted device.

39. An auditory prosthesis according to any one of claims 33 to 38, wherein said first sensor means are arranged so as to electrically sense activity of the stapedius muscle.

40. An auditory prosthesis according to claim 33, wherein said stimulation device includes a multielectrode array, said array characterizing channels, wherein said processor generates stimulus signals for each of said channels in accordance with a maximum comfortable stimulation level for each of said channel wherein said processor is constructed and arranged to determine said maximum comfortable stimulation levels separately for each of said channels during said dynamic range setting procedure.

41. An auditory prosthesis according to claim 33 wherein second sensor is constructed and arranged to sense the neural response to said stimulus signals from one of an auditory nerve and a basilar membrane of the user.

42. A method for automatically setting threshold stimulation levels and maximum comfortable stimulation levels in a multichannel auditory prosthesis, said prosthesis including an implanted stimulation device, memory means, first sensor means for detecting electrical activity associated with the stapedius muscle, and second sensor means for detecting an electrical response of nervous tissue to stimulation, including the steps for each channel, which may be performed in any suitable order, of (a) providing stimulus signals from a predefined level and gradually increasing the amplitude until a predefined neural response is detected by said second sensor means,using the amplitude at that point to determine a threshold stimulation level value, and storing said value in said memory means; and (b) providing stimulus signals at a predefined lower limit and gradually increasing amplitude of said signal until a predefined level of stapedius activity is detected by said first sensor means, the amplitude at that point being used to determine a maximum comfortable stimulation level value, and storing said value in said memory means.

43. A cochlear implant for implantation into a patient, said patient having a cochlea and a stapedius muscle, said cochlear implant comprising:

a microphone sensing ambient sounds and generating corresponding sound signals;

a processor receiving said sound signals and generating corresponding stimulation signals in accordance with at least one operational parameter;

an electrode extending into said cochlea for applying said stimulation signals; and a stapedius sensor for sensing an attribute of said stapedius muscle and generating a stapedius muscle signal indicative of said attribute;

wherein said processor is adapted to modify said operational parameter in accordance with said stapedius muscle signal.

44. The cochlear implant of claim 43 further comprising a nerve sensor for sensing electrical activity in the patient's aural nerve.

45. The cochlear implant of claim 43 wherein said processor is constructed and arranged to receive inputs from said stapedius and nerve sensors and to automatically determine a minimum stimulation threshold and a maximum stimulation threshold for the patient based on said inputs.

46. Th cochlear implant of claim 43 wherein said processor includes a parameter calculator for calculating a stimulation threshold based on the input from said stapedius sensor.

* * * * *